(12) United States Patent
Barth et al.

(10) Patent No.: US 6,566,533 B1
(45) Date of Patent: May 20, 2003

(54) METHOD OF PRODUCING HETEROCYLIC CARBAMATES FROM AZA-HETEROCYCLIC COMPOUNDS AND CARBON DIOXIDE

(75) Inventors: Hubert Barth, Emmendingen (DE); Klaus Steiner, Emmendingen (DE); Simon Schneider, Merzhausen (DE); Ulrich Bayer, Ulm (DE); Manfred Westermayer, Gundelfingen (DE); Ulrike Wolfsperger, Gundelfingen (DE); Hans-Jürgen Betche, Vörstetten (DE)

(73) Assignee: Warner-Lambert Company LLC, Morris Plains, NJ (US)

( * ) Notice: Subject to any disclaimer, the term of this patent is extended or adjusted under 35 U.S.C. 154(b) by 0 days.

(21) Appl. No.: 09/869,872
(22) PCT Filed: Feb. 25, 2000
(86) PCT No.: PCT/EP00/01573
§ 371 (c)(1),
(2), (4) Date: Jul. 6, 2001
(87) PCT Pub. No.: WO00/58286
PCT Pub. Date: Oct. 5, 2000

(30) Foreign Application Priority Data

Mar. 25, 1999 (DE) .......................................... 199 13 483

(51) Int. Cl.[7] .............................................. C07D 209/00
(52) U.S. Cl. ........................................ 548/441; 548/510
(58) Field of Search ................................. 548/441, 510

(56) References Cited

U.S. PATENT DOCUMENTS 5,792,865 A  8/1998  Flood et al. ................. 544/194

FOREIGN PATENT DOCUMENTS

EP   0628542    12/1994
WO   9804531    2/1998

OTHER PUBLICATIONS

Weedon and Zhang, "Removable Groups for Activation of Indole Photochemistry", *Synthesis*, 1992, pp 95–100.
Illi, "Phasentransfer–katalysierte N–Acylierung von Indol", *Synthesis*, 1979, pp 387–388.
Butcher, "Carbamate esters: a simple, mild method of formation", *Synlett*, 1994, pp 825–826.
Boger and Patel, "Indole N–Carbonyl Compounds: Preparation and Coupling of Indole–1–carboxylic Acid Anhydride", *J. Org. Chem.*, vol. 52, No. 17, 1987, pp 3934–3936.
Macor et al., "Neutral Acylation (Protection) of the Indole Nitrogen: A Simple Synthesis of Indole–1–Carboxylates, Indole–1–Thiocarboxylates and Indole–1–Baboxamides", *Tetrahedron Letters*, vol. 40, 1999, pp 2733–2736.

*Primary Examiner*—Bruck Kifle
(74) *Attorney, Agent, or Firm*—Charles W. Ashbrook; Matthew J. Russo

(57) ABSTRACT

The invention relates to a method of producing heterocyclic carbamates of the general formula (I) by reacting aza-heterocyclic compounds with alkyl- or aryl-halides in the presence of carbon dioxide and alkali carbonate, and to new compounds of the general formula (I).

6 Claims, No Drawings

METHOD OF PRODUCING HETEROCYLIC CARBAMATES FROM AZA-HETEROCYCLIC COMPOUNDS AND CARBON DIOXIDE

The present invention concerns a process for the preparation of compounds of the general formula I

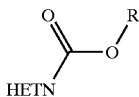

I in which HETN signifies an aromatic aza-heterocycle with, in all, 5 or 6 ring atoms, whereby up to 3 ring atoms are nitrogen atoms, whereby up to two further aromatic carbon ring atoms can be condensed on the heterocycle and R signifies a straight-chained or branched alkyl group with 1 to 10 C-atoms, a benzyl group unsubstituted or substituted with up to three $C_{1-4}$ alkyl groups, $C_{1-4}$ alkoxy groups, halogen atoms, with a cyano group, a nitro group, a trifluoromethyl group or an alkoxycarbonyl group with up to 4 C-atoms, an aralkyl group or an alkenyl group. The term aralkyl group includes a lower alkyl radical with 2 to 10 C-atoms, wherein up to two H atoms are replaced by phenyl groups, which possibly in turn can be substituted with $C_{1-4}$ alkyl group, a $C_{1-4}$ alkoxy group, a cyano group, nitro group, a trifluoromethyl group, an alkoxycarbonyl group with up to 4 C-atoms or with up to three halogen atoms. The term alkenyl characterises an unsaturated hydrocarbon radical with up to 5 C-atoms.

Carbamates play a large part in many fields of chemistry, i.e. in the synthesis of medicaments (B. J. Ludwig, L. S. Powell, F. M. Berger, J. Med. Chem. 12, 462, 1969) or of plant protection agents (E. Bocker, W. Draber in: R. Wegler, Chemie der Pflanzenschutz und Schädlingsbekämpfungsmittel, Vol. 1, P. 220, Springer, Berlin, Heidelberg, New York 1970; Ullmann's Encyclopedia of Industrial Chemistry, 5th ed., Vol. A5, p. 51, VCH Verlagsgesellschaft mbH, 1986).

Since some carbamide esters, depending upon the ester radical, can again be split by special reagents, their synthesis, also in protective group chemistry, is an important process for the reversible blocking of amine functions, especially in heterocycle chemistry and in peptide chemistry (P. J. Kocienski, Protecting Groups, THIEME Verlag Stuttgart, 1994; Theodora W. Greene, P. G. M. Wuts, Protective Groups in Organic Synthesis, John Wiley & Sons, New York, 1991).

Open-chained carbamic acid esters can also be prepared by many processes (U. Petersen in HOUBEN-WEYL, Methoden der Organischen Chemie, Volume E4, Kohlensäure Derivate, p. 149 ff, Georg Thieme Verlag, Stuttgart, New York 1983). A frequently used method in the case of the protection of aza-heterocycles consists in the conversion of the aromatic NH group of the aza-heterocycle with the help of a chloroformic acid ester of the general formula I (scheme 1):

Scheme 1

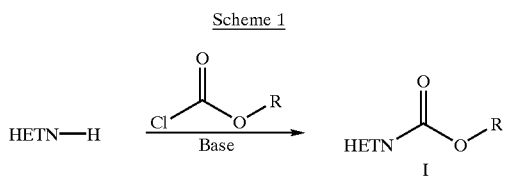

Thus, in the case of the preparation of indole-N-carboxylic acid from indole and carbon dioxide (D. L. Boger, J. Org. Chem. 52, 3934, 1987) or of indole-N-carbamates from indole and chloroformic acid esters (A. C. Weedon, B. Zhang, Synthesis 1992, 95; E. Reimann, T. Hassler, H. Letter, Arch. Pharm. 323, 255, 1990), as base there is frequently used hydrolysis sensitive butyl lithium, dissolved in an inert solvent or, however, there find use quite special processes, such as e.g. phase transfer-catalysed reactions (A. C. Weedon, B. Zhang, Synthesis 1992, 95; E. Reimann, T. Hassler, H. Letter, Arch. Pharm. 323, 255, 1990).

Stimulated by the work of Ken J. Butcher for the preparation of carbamate esters from amines and carbon dioxide (Ken J. Butcher, Synlett 1994, 825), we investigated whether aza-heterocycles of the general formula II can be converted into heterocyclic carbamate esters of the general formula I (scheme 2) with use of carbon dioxide, alkali metal carbonate, especially caesium carbonate, and alkyl or arylhalides of the general formula III

HETN-H                    II

R-HAL                     III whereby HETN and R possess the above-mentioned meaning and HAL stands for chlorine, bromine or iodine:

Scheme 2

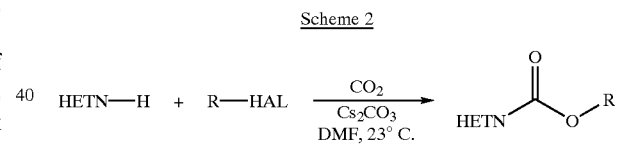

Since the above-mentioned aza-heterocycles of the general formula II are, because of their physical and chemical properties, set to be counted with the classical amines and, as a rule, are more strongly acidic in comparison with the amines used by Ken J. Butcher, such as e.g. piperidine, benzylamine, N-methylbenzylamine and aniline, it was not to be expected that, in the case of carrying out of the reaction according to scheme 2 with use of azaheterocycles of the general formula II, heterocyclic carbamate esters of the general formula I would result. If one carries out the reaction as described by Ken J. Butcher with use of indole, caesium carbonate and benzyl bromide, then one finds only traces of the desired product, N-benzyloxycarbonylindole.

Surprisingly, however, it was found that carbamate esters of the general formula I can, nevertheless, be prepared under very mild and preparatively very simple conditions when one increases the amounts of the alkali metal carbonate used, especially caesium carbonate (2 to 4 equivalents, referred to the aza-heterocycle) and the amounts of alkyl or aryl halide (1.2 to 2 equivalents, referred to the aza-heterocycle) and, above all, prolongs the reaction time of 24 hours to 48 to 72 hours.

The preparative procedure is very simple and takes place as follows:

The aza-heterocycle and a 2 to 4 fold molar excess of alkali metal carbonate, especially caesium carbonate, are placed in a suitable dipolar aprotic solvent, such as e.g. dimethylformamide, acetonitrile, dimethylacetamide or N-methylpyrrolidone, at room temperature. With good stirring, carbon dioxide gas is now passed into the reaction mixture at room temperature with exclusion of moisture for 4 to 6 hours. The carbon dioxide gas stream is hereby produced by allowing dry ice to evaporate at room temperature which is present in an Erlenmeyer flask which is connected with the reaction vessel via a gas inlet pipe. One now adds to the reaction mixture in one portion the alkyl or aryl halide of the general formula III in question dissolved in a little solvent, passes in further carbon dioxide for 1 to 2 hours, again adds thereto about 10% to 100%, preferably 30% of the original amount of alkyl or aryl halide and then closes the reaction vessel. With closed reaction vessel, one now further stirs for 24 hours to 4 days, preferably 3 days, at room temperature. Thereafter, one pours the reaction mixture on to water, extracts the product with ethyl acetate, and purifies the crude product obtained after removal of the extraction agent with the methods usual in preparative organic chemistry, e.g. by chromatography on silica gel or crystallisation. Preferred solvent of the described reaction is dimethylformamide. Preferred alkali metal carbonate is caesium. carbonate.

The reaction conditions are very mild, many functional groups, such as e.g. the double bond, the nitro group, the alkoxycarbonyl group, the cyano group, halogen groups and alkoxy groups on aromatics are tolerated. The starting materials—aza-heterocycles and alkyl and aryl halides—are commercially available in large number. The conditions for the working up of the reaction are very simple to produce.

Under the assumption that caesium carbonate can be produced again from the extracted aqueous residue, the method is suitable to bind gaseous carbon dioxide on to simple commercially available starting materials, such as aza-heterocycles, especially indole and alkyl/aryl halides and thereby to produce valuable, energy-rich intermediate products.

In this sense, the said process is a valuable contribution to an environmentally-friendly chemistry.

On the basis of a simple practical carrying out of the reaction, the process procedure is also outstandingly suitable for a high throughput synthesis of heterocyclic carbamates since, by suitable combination of aza-heterocycles and alkyl or aryl halides in a carbon dioxide gasification apparatus, a plurality of synthesis reactions can take place in parallel.

Many of the compounds synthesised by the described process are new, their testing for suitability of use in the field of medicinal chemistry and plant protection chemistry is still outstanding.

The invention is illustrated and explained by the following embodimental examples.

EXAMPLE 1

N-benzyloxycarbonylindole from indole and benzyl bromide.

Into a suspension of 0.48 g indole and 3.2 g caesium carbonate in 30 ml dry dimethylformamide, which is present in a 50 ml three-necked flask, is passed carbon dioxide gas for 6 hrs. with good stirring at room temperature. The carbon dioxide gas stream is produced by allowing solid carbon dioxide (dry ice) to evaporate which is present in a 500 ml Erlenmeyer flask which is connected with the reaction apparatus via a gas inlet pipe. One adds thereto 0.7 g benzyl bromide, dissolved in a little DMF, passes in further carbon dioxide gas for 1.25 hrs., again adds 0.2 g benzyl bromide thereto and closes the reaction vessel airtight. The reaction mixture is now further stirred for 2 days at room temperature. Thereafter, one pours the reaction mixture on to 50 ml water (care: exothermic reaction) and extracts the product 3 times with, in each case, 50 ml ethyl acetate. The combined organic phases are evaporated on a rotavapor. The dimethylformamide present in the oily residue together with the product is removed on the rotavapor by azeotropic distillation by means of toluene at 40 mbar/50° C. The residue is chromatographed on 130 g silica gel (0.040–0.063 mm) with toluene as elution agent. One obtains 1.1 g of product (99%), m.p. 420C.

The following Examples were carried out analogously to Example 1. There are given the reaction times in hours/the eluent for the chromatography/the yield and/physical properties.

EXAMPLE 2

N-tert.-Butoxycarbonylindole from indole and tert.-butyl bromide (2 mol bromide) 64/toluene/6.7%/oil

EXAMPLE 3

N-Ethoxycarbonylindole from indole and ethyl bromide (2 mol bromide) 14/toluene/71%/oil

EXAMPLE 4

N-Benzyloxycarbonylindole from indole and benzyl bromide with use of potassium carbonate as base 64/toluene/64%/m.p. 42° C.

EXAMPLE 5

5-Benzyloxy-N-benzyloxycarbonylindole from 5-hydroxyindole and benzyl bromide (3 mol bromide) 24/crystallisation in the evaporation of the ethyl acetate extract/82.9%/m.p. 144° C.

EXAMPLE 6

5-Hydroxy-N-benzyloxycarbonylindole from 5-hydroxyindole and benzyl bromide (2 mol bromide) 48/toluene-ethanol 10+2/33%/m.p. 107°–109° C.

EXAMPLE 7

N-Allyloxycarbonylindole from indole and allyl bromide (2 mol bromide) 24/hexane-ethyl acetate 10+2/98%/oil

EXAMPLE 8

5-Chloro-N-benzyloxycarbonylindole from 5-chloroindole and benzyl bromide (2 mol bromide) 64/crystallisation in the evaporation of the ethyl acetate extract/96%/m.p. 68° C.

EXAMPLE 9

5-Benzyloxy-N-benzyloxycarbonylindole from 5-benzyloxyindole and benzyl bromide 64/crystallisation of the product in the evaporation of the ethyl acetate extract/75%/m.p. 144° C.

The same batch with use of potassium carbonate: 64/crystallisation/75.6%/m.p. 144° C.

EXAMPLE 10

5-Methyl-N-benzyloxycarbonylindole from 5-methylindole and benzyl bromide 64/toluene/98%/m.p. 63°–64° C.

EXAMPLE 11

5-Fluoro-N-benzyloxycarbonylindole from 5-fluoroindole and benzyl bromide 64/hexane-ethyl acetate 10+2/98%/m.p. 50° C.

EXAMPLE 12

5-Methoxy-N-benzyloxycarbonylindole from 5-methoxyindole and benzyl bromide 64/toluene/97%/m.p. 65° C.

EXAMPLE 13

5-Bromo-N-benzyloxycarbonylindole from 5-bromoindole and benzyl bromide 64/hexane-ethyl acetate 10+2/98%/m.p. 69° C.

EXAMPLE 14

5,6-Dimethoxy-N-benzyloxycarbonylindole from 5,6-dimethoxyindole and benzyl bromide 64/hexane-ethyl acetate 1+1/98%/m.p. 110° C.

EXAMPLE 15

5-Nitro-N-benzyloxycarbonylindole from 5-nitroindole and benzyl bromide 30/hexane-ethyl acetate 1+1/74%/m.p. 120° C.

EXAMPLE 16

5,6-Methylenedioxy-N-benzyloxycarbonylindole from 5,6-methylenedioxyindole and benzyl bromide 30/toluene/96%/m.p. 116–117° C.

EXAMPLE 17

N-propyloxycarbonylindole from indole and n-propyl bromide (2 mol bromide) 64/hexane-ethyl acetate 10+2/90%/oil

EXAMPLE 18

N-4-Methoxybenzyloxycarbonylindole from indole and 4-methoxybenzyl chloride 64/hexane-ethyl acetate 10+2/95%/m.p. 80° C.

EXAMPLE 19

N-2,4-Dichlorobenzyloxycarbonylindole 15 from indole and 2,4-dichlorobenzyl chloride 64/hexane-ethyl acetate 10+2/91%/m.p. 96° C.

EXAMPLE 20

N-2-Phenylethyloxycarbonylindole from indole and 2-phenylethyl bromide 20 64/hexane-ethyl acetate 10+2/46%/oil

EXAMPLE 21

N-4-Methylbenzyloxycarbonylindole from indole and 4-methylbenzyl chloride 64/hexane-ethyl acetate 10+2/73.5%/m.p. 73–76° C.

EXAMPLE 22

N-4-Chlorobenzyloxycarbonylindole from indole and 4-chlorobenzyl chloride 64/hexane-ethyl acetate 10+2/m.p. 77° C.

EXAMPLE 23

N-isopropyloxycarbonylindole from indole and isopropyl bromide (2 mol bromide) 64/hexane-ethyl acetate 10+2/36%/oil

EXAMPLE 24

N-Benzyloxycarbonylindole from indole and benzyl bromide in acetonitrile 64/toluene/97%/43° C.

EXAMPLE 25

7-Methyl-N-benzyloxycarbonylindole from 7-methylindole and benzyl bromide 64/toluene/64.3%/m.p. 20° C.

EXAMPLE 26

2-Methyl-N-benzyloxycarbonylindole from 2-methylindole and benzyl bromide 24/toluene/92%/m.p. 54° C.

EXAMPLE 27

N-Methoxycarbonylindole from indole and methyl iodide (2 mol iodide) 64/hexane-ethyl acetate 10+2/91.8%/oil

EXAMPLE 28

5-Cyano-N-benzyloxycarbonylindole from 5-cyanoindole and benzyl bromide 64/toluene/79.4%/oil

EXAMPLE 29

3-Ethoxycarbonylmethyl-N-benzyloxycarbonylindole from 3-ethoxycarbonylmethylindole and benzyl bromide 64/toluene-ethanol 10+0.5/93.2%/oil

EXAMPLE 30

3-Methoxycarbonyl-N-benzyloxycarbonylindole from indole-3-carboxylic acid methyl ester and benzyl bromide 64/hexane-ethyl acetate 1+1/37.8%/m.p. 88° C. (65% 3-methoxycarbonyl-N-benzylindole)

EXAMPLE 31

3-Cyanomethyl-N-benzyloxycarbonylindole from 3-cyanomethylindole and benzyl bromide 64/toluene-ethanol 10+0.5/88.2%/m.p. 95° C.

EXAMPLE 32

3-(2-Benzyloxyethyl)-N-benzyloxycarbonylindole from 3-(2-hydroxyethyl)-indole and benzyl bromide (2.5 mol bromide) 64/hexane-ethyl acetate 10+2/96.5%/oil

EXAMPLE 33

N-2-nitrobenzyloxycarbonylindole from indole and 2-nitrobenzylbromide 64/toluene/87.2%/m.p. 106° C.

EXAMPLE 34

3-Ethoxycarbonylvinyl-N-benzyloxycarbonylindole from indole-3-acrylic acid ethyl ester and benzyl bromide 64/hexane-ethyl acetate 10+2/34.9%/m.p. 96° C.

EXAMPLE 35

5-Methoxycarbonyl-N-benzyloxycarbonylindole from indole-5-carboxylic acid methyl ester and benzyl bromide 64/toluene/100%/m.p. 88° C.

EXAMPLE 36

(±)-N-1-Phenylethyloxycarbonylindole from indole and (±)-1-phenylethyl bromide 64/toluene/91.9%/oil

EXAMPLE 37

N-Benzyloxycarbonylimidazole from imidazole and benzyl bromide 60/toluene-ethanol 10+2/8.4%/oil

EXAMPLE 38

N-Benzyloxycarbonylindazole from indazole and benzyl bromide 64/hexane-ethyl acetate 10+2/74.4%/m.p. 84° C.

EXAMPLE 39

N-Benzyloxycarbonylbenzimidazole from benzimidazole and benzyl bromide 64/hexane-ethyl acetate 1+1/24.1%/m.p. 71–72° C.

EXAMPLE 40

4-Phenyl-N-benzyloxycarbonylimidazole from 4-phenylimidazole and benzyl bromide 64/toluene-ethanol 10+2/21.9%/m.p. 28° C.

EXAMPLE 41

N-Benzyloxycarbonylpyrrole from pyrrole and benzyl bromide 64/toluene/96%/m.p. 28° C.

EXAMPLE 42

N-Benzyloxycarbonylcarbazole from carbazole and benzyl bromide 24/crystallisation after evaporation of the ethyl acetate extract/98%/m.p. 74° C.

SUMMARY

The invention concerns a process for the preparation of heterocyclic carbamates of the general formula I

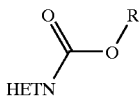

I by reaction of aza-heterocycles with alkyl or aryl halides with use of carbon dioxide, alkali metal carbonate, as well as new compounds of the general formula I.

What is claimed is:

1. A process for preparing a heterocyclic carbamate of formula I

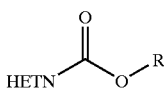

I in which HETN signifies an indole or a carbazole having a ring nitrogen that is bonded to a —C(O)—O—R group in formula I and R signifies a straight-chained or branched alkyl group with 1 to 10 C-atoms, a benzyl group unsubstituted or substituted with up to three $C_{1-4}$ alkyl groups, $C_{1-4}$ alkoxy groups, halogen atoms, with a cyano group, a nitro group, a trifluoromethyl group or an alkoxycarbonyl group with up to 4 C-atoms, an aralkyl group or an alkenyl group, the process comprising converting an aza-heterocycle of formula II

HETN—H     II into a heterocyclic carbamate of formula I using carbon dioxide, an akali metal carbonate and an alkyl or aryl halide of formula III

R—HAL     III wherein HETN and R in formula II and formula III possess the above-mentioned meaning, HAL stands for chlorine, bromine or iodine, the ring nitrogen of HETN in formula II is bonded to a hydrogen atom, and carbon dioxide is provided from a source that is different than, or in addition to, carbon dioxide in ambient air.

2. The process of claim 1, further comprising a solvent selected from the group consisting of dimethylformamide, acetonitrile, dimethylacetainide, and N-methylpyrrolidone, or mixtures thereof.

3. The process of claim 1, further comprising passing carbon dioxide gas into a reaction batch containing the aza-heterocycle of formula II.

4. The process of claim 1, further comprising:

placing the aza-heterocycle of formula II in a solvent with an excess of caesium carbonate to form a reaction mixture;

passing carbon dioxide gas through the reaction mixture;

adding the halide of formula III to the reaction mixture; and stirring the reaction mixture in a closed vessel following the addition of the halide.

5. The process of claim 4, further comprising placing the aza-heterocycle of formula II in a solvent with a 2- to 4-fold excess of caesium carbonate.

6. The process of claim 4, further comprising adding the halide of formula III to the reaction mixture in at least two additions.

* * * * *